United States Patent [19]

Gray et al.

[11] Patent Number: 4,513,149
[45] Date of Patent: Apr. 23, 1985

[54] RANEY NICKEL ALLOY EXPANDED MESH HYDROGENATION CATALYSTS

[75] Inventors: Thomas J. Gray, Guilford; Norman G. Masse, Wallingford, both of Conn.

[73] Assignee: Olin Corporation, Cheshire, Conn.

[21] Appl. No.: 365,210

[22] Filed: Apr. 5, 1982

[51] Int. Cl.³ .................. C07C 85/24; C07C 85/00
[52] U.S. Cl. ........................... 564/449; 564/450; 585/270
[58] Field of Search ............... 564/449, 450; 585/270

[56] References Cited

U.S. PATENT DOCUMENTS

| | | | |
|---|---|---|---|
| 2,092,525 | 9/1937 | Adkins et al. | 564/450 |
| 2,606,925 | 8/1952 | Whitman | 564/449 |
| 2,716,135 | 8/1955 | Winstrom | 260/580 |
| 2,945,063 | 7/1960 | Quinn et al. | 564/449 |
| 2,948,687 | 8/1960 | Hadley | 252/470 |
| 3,032,586 | 5/1962 | Dierichs et al. | 260/580 |
| 4,153,578 | 5/1979 | De Thomas et al. | 252/438 |

OTHER PUBLICATIONS

Barton Milligan and Kevin E. Gilbert, "Diaminotoluenes", *Kirk–Othmer Encyclopedia of Chemical Technology*, Third Edition, vol. 2, 1978, pp. 321–329.

*Primary Examiner*—Paul F. Shaver
*Attorney, Agent, or Firm*—Donald F. Clements; James B. Haglind

[57] ABSTRACT

Hydrogenation processes utilizing improved Raney nickel alloy catalysts are disclosed. The catalyst comprises a monolithic mesh type structure of a nickel alloy having an integral Beta phase Raney $Ni_xM_{1-x}$ coating on its outer surfaces, where M is a catalytic activator selected from the group consisting of molybdenum, ruthenium, tantalum and titanium and where x, the weight fraction of nickel in the combined alloy, is between about 0.80 and about 0.95. The catalyst is effective in processes for hydrogenation of aromatic compounds of the type

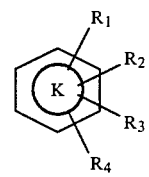

wherein K is either benzene or naphthalene, $R_1$ is a hydrogen atom or an aliphatic chain containing from about 1 to about 9 carbon atoms or a phenyl radical, $R_2$ is a hydrogen atom or an aliphatic chain containing from about 1 to about 3 carbon atoms, and $R_3$ and $R_4$ are hydrogen atoms, hydroxy, or nitro groups. When this catalyst is used, substantially higher reactant flow rates and lower operating temperatures are possible as compared to conventional fluidized bed granular catalysts.

40 Claims, 7 Drawing Figures

FIG-1

ALUMINIZED MESH
AFTER NaOH LEACH

RANEY NICKEL ALLOY EXPANDED MESH HYDROGENATION CATALYSTS

BACKGROUND OF THE INVENTION

This invention relates to Raney nickel alloy catalysts useful for hydrogenation reactions.

Raney nickel is a well-known hydrogenation catalyst which was described originally in U.S. Pat. No. 1,638,190 issued to Raney on May 10, 1927. Raney nickel is prepared by alloying nickel and aluminum and leaching out the aluminum with alkali to expose nickel as a finely divided porous solid in which form nickel is an effective hydrogenation catalyst.

Subsequently, improved nickel catalysts have been provided in the art by alloying various metallic constituents with the nickel and aluminum prior to the treatment with alkali. For example, in U.S. Pat. No. 2,948,687 issued to Hadley on Aug. 9, 1960, molybdenum is alloyed with nickel and aluminum and treated with alkali to provide a nickel-molybdenum alloy catalyst. The use of such catalysts either as finely divided powders or precipitated onto a support structure such as $Al_2O_3$ is well known and such catalysts are widely used at the present time. However, it is also recognized that the use of these catalysts in either fixed bed or fluidized bed operations carries with them a number of constraints. For example, it is known that many of them are quite sensitive to small amounts of sulfur or carbon monoxide contamination in the feedstock. Also, when used in fluidized bed operations, the feedstock is subject to rather large pressure drops so that fairly rugged equipment is needed to move it through the bed. Lastly, many of these catalysts are sufficiently active so that if overheated during the reaction they will crack the carbonaceous feedstock and form coke on their surfaces with resultant significant decreases in activity. What is needed is a catalyst which, while retaining all of the advantages of high activity shown by Raney nickel, is not significantly affected by such operating conditions.

SUMMARY OF THE INVENTION

It is the object of this invention to provide an improved Raney nickel alloy catalyst which performs effectively in different catalytic hydrogenation processes.

It is a further object of this invention to provide an improved Raney nickel alloy catalyst which is relatively insensitive to the presence of sulfur and carbon monoxide in the feedstock.

It is still a further object of this invention to provide an improved Raney nickel alloy catalyst which does not produce a high pressure drop in the system wherein it is used.

The present invention provides an improved monolithic Raney hydrogenation catalyst for use in hydrogenation reactions, said catalyst being comprised of an integral Raney metal alloy surface layer on a selected alloy substrate mesh structure wherein said surface layer is predominantly derived from an adherent Beta structured crystalline precursor outer portion of said structure.

Another embodiment of the invention is provided by the use of a monolithic Raney hydrogenation catalyst comprised of an integral Raney metal alloy surface layer on a metallic mesh substrate, said Raney metal alloy surface being predominantly derived from an adherent $Ni_xM_{1-x}Al_3$ Beta structured crystalline precursor surface layer, where M is a catalytic activator selected from the group consisting of molybdenum, titanium, tantalum and ruthenium and where x, the weight fraction of nickel in the combined NiM alloy, is from about 0.80 to about 0.95.

The invention further comprises a method of using said monolithic Raney catalyst in hydrogenation reactions wherein said catalyst is produced by

(a) coating with aluminum the surfaces of a clean, non-porous perforated metal base structure of an alloy comprising from about 20 to about 5 percent by weight of a catalytic activator selected from the group consisting of molybdenum, titanium, tantalum, and ruthenium, and from about 80 to about 95 percent by weight of nickel;

(b) heating said coated surfaces by maintaining said surfaces at a temperature of from about 660° C. to about 750° C. for a time sufficient to infuse a portion of said aluminum into outer portions of said structure to produce an integral alloy layer of nickel, the catalytic activator and aluminum in said outer portions predominantly of Beta structured grains, but insufficient in time to create a predominance of Gamma structured grains in said outer portions; and (c) leaching out residual aluminum and intermetallics from the alloy layer until a Raney nickel-catalytic activator alloy layer is formed integral with said structure.

These and other objects of this invention will become apparent from the following description and the appended claims.

The Raney nickel-catalytic activator alloy catalysts of this invention have been utilized as catalysts in the hydrogenation of aromatic compounds of the type wherein K is either benzene or naphthalene, $R_1$ is a hydrogen atom or an aliphatic chain containing from about 1 to about 9 carbon atoms or a phenyl radical; $R_2$ is a hydrogen atom or an aliphatic chain containing from about 1 to about 3 carbon atoms, and $R_3$ and $R_4$ are hydrogen atoms, hydroxy, or nitro groups. One process of particular interest within this group is the saturation of aromatic olefinic double bond linkages and more particularly the conversion of single and polynuclear aromatic compounds such as benzene toluene, xylene; naphthalene, etc., into the corresponding saturated alicyclic compounds. Another is the conversion of aromatic nitro groups ($-NO_2$) to amine groups ($-NH_2$). Still another is the combination of these reactions so that an aromatic nitro compound such as dinitrotoluene is directly converted into the corresponding alicyclic amine compound—diaminomethylcyclohexane.

It has been found that the catalyst of the present invention is applicable to all of these processes in a manner which is substantially advantageous when compared to prior art catalysts used for these purposes.

DETAILED DESCRIPTION OF THE PREFERRED EMBODIMENTS

This invention is described in terms of the preparation and use of a monolithic Raney nickel alloy catalyst having about 5 to about 20 percent by weight of molybdenum therein. It should be understood that the molybdenum may be replaced in whole or in part by ruthenium, titanium, tantalum or mixtures thereof in the broader aspects of the invention.

CATALYST PREPARATION

Figure 1:
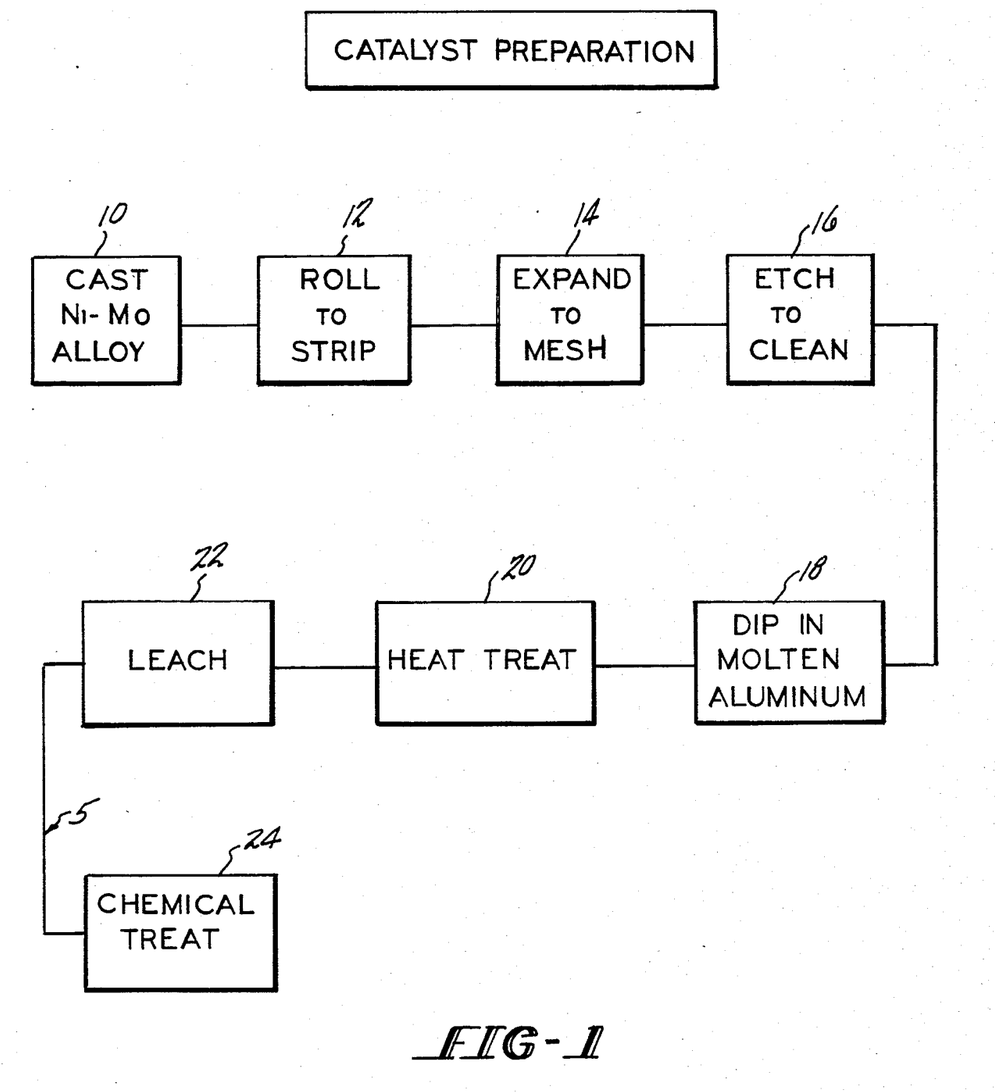
FIG. 1 is a flow diagram of a process for the preparation of an expanded mesh embodiment of the catalyst as used in the present invention.

Catalyst (5) of the present invention is prepared as shown in FIG. 1. The integral Raney nickel alloy surface of the monolithic catalyst (5) of this invention is formed on a supportive nickel bearing core or substrate. While cores of substantially pure nickel or an appropriate nickel bearing alloy such as Inconel 600, Hastelloy C or 310 stainless steel can be used, it is preferred to have the outer portions of the core (core is used interchangeably herein with substrate) itself serve as the nickel bearing alloy outer layer. Where cores of other materials or alloys are used, a nickel alloy coating of the desired composition should first be deposited onto the surfaces thereof by a variety of known techniques such as metal dipping, electroplating, electroless plating and the like. This coating should be at least 100 microns and preferably at least 150 microns thick. This helps to substantially improve the thermal stability of the coating by making the transition across the coating/substrate interface much less abrupt and thus greatly reducing tensile stresses and the possibility of corrosion and subsequent failure at this interface.

Accordingly, the core material for the catalyst of the present invention comprises an alloy in which nickel and the selected alloying material are melted together to form a precursor ingot (10) having the desired composition. The preferred alloy weight percentage for the molybdenum component is between about 10 and about 18; for ruthenium, it is betweeen about 5 and about 10 percent; for tantalum, it is between about 5 and about 15 percent; and for titanium, it is between about 5 and about 10 percent. The cast ingot is then rolled out to form a sheet or strip (12) preferably in the thickness range of between about 0.01 and about 0.02 inch.

While support for the catalyst of the current invention can be in the form of any conveniently shaped structure, a perforated metal base, particularly an expanded metal screen or mesh (14), is preferred. Such an open structure is found to be a significant factor in providing a catalytic process having substantial life-time and operational advantages over other types of catalytic structures used for this purpose. The final mesh which is prepared by conventional metal expansion techniques forms a regularly shaped diamond or square celled structure typically having cells on the order of 0.2 to 0.3 inch on a side. The thickness and mesh opening values are not critical and, depending on such factors as alloy composition and reaction parameters, other cell sizes could easily be used.

Prior to further processing, expanded mesh (14) is thoroughly cleaned by conventional means, such as degreasing, acid etching and/or grit blasting (16) to remove surface contaminates and thus improve the wetting of the subsequently applied aluminum to the surface.

Formation of the catalyst begins when this clean surface is subjected to an aluminizing treatment (18). By "aluminizing", as used herein, it is meant that aluminum is brought into intimate contact with the cleaned nickel bearing alloy material at the surface of the core so that when heat-treated at interdiffusion step (20), the desrred nickel alloy-aluminum alloy layer is formed. This can be accomplished by any of several known methods such as flame or plasma spraying the aluminum onto the surface of the core, dipping the core into molten aluminum or by the use of fused salt electrolysis, with dipping being preferred.

Whichever method of aluminizing is used, an aluminum layer of at least 100-micron thickness should be deposited on the surface of the core. Much thicker aluminum layers of, for example, greater than 500-micron thickness, perform satisfactory in the process but for reasons for economy, aluminum layer thicknesses of between about 150 and about 300 microns are preferred. With dipping, such a thickness is achieved in a time of between about 0.5 and about 5.0 minutes when the aluminum is between about 600° C. and about 700° C.

Interdiffusion step or heat treat step (20) is carried out at a temperature of at least about 660° C., i.e., above the normal melting point of aluminum. However, to drive the interdiffusion process at a reasonable rate, higher temperatures should be used, with the temperature within the range of from about 700° C. to about 750° C. and particularly from about 715° C. to about 735° C. being most preferred. Usually interdiffusion is carried out in an atmosphere of hydrogen, nitrogen or an inert gas to prevent oxidation of the surface. This interdiffusion heat treatment is continued for a time sufficient for the aluminum and nickel alloy to react to form a nickel alloy-aluminum ternary alloy of at least about 40 microns and preferably at least about 80 microns in thickness. Interdiffusion times within the range of from about 5 to about 30 minutes satisfy this need. For nickel-molybdenum, interdiffused alloy layers of about 100 to about 400 microns in thickness are preferred, with best results obtained with a thickness from about 150 to about 300 microns.

During heat treatment at temperatures above about 660° C. excessively long interdiffusion times, e.g. 1 hour or more, and excessively high temperatures, should be avoided for technical as well as economic reasons. For example, at temperatures above about 855° C., the Beta phase quickly transforms into liquid and Gamma phase. Further, if interdiffusion at any temperature is continued too long, especially at interdiffusion temperatures of much above about 800° C., the intermetallic NiAl (Eta phase) forms which is quite resistant to subsequent leaching of the aluminum so that a satisfactory Raney surface will not form.

Lastly, for coatings on a substrate differing in composition from the coating, extended heat treatments can damage the substrate or form undesirable brittle intermetallics at the coating substrate interface. For example, if aluminum is diffused into a nickel alloy coated steel core, excessive interdiffusion time or temperature can result in the aluminum "breaking through" to diffuse into the steel base of the core. This results in the formation of a very brittle $FeAl_3$ intermetallic phase which will significantly undermine the strength of the bond between the core and the interdiffused layer.

By providing sufficient quantities of aluminum and nickel, while avoiding excessively long treatments or excessively high temperatures during interdiffusion, breakthrough and formation of the undesired intermetallics are avoided.

Figure 3:
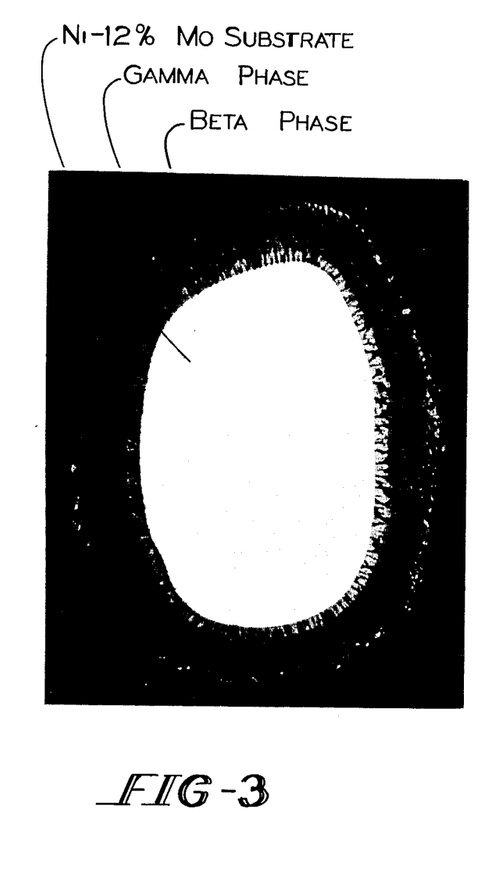
FIG. 3 is a 250× photomicrograph of a section of the mesh embodiment of the catalyst of FIG. 2 showing a Raney Ni—Mo layer after heat treatment and leaching.
Figure 4:
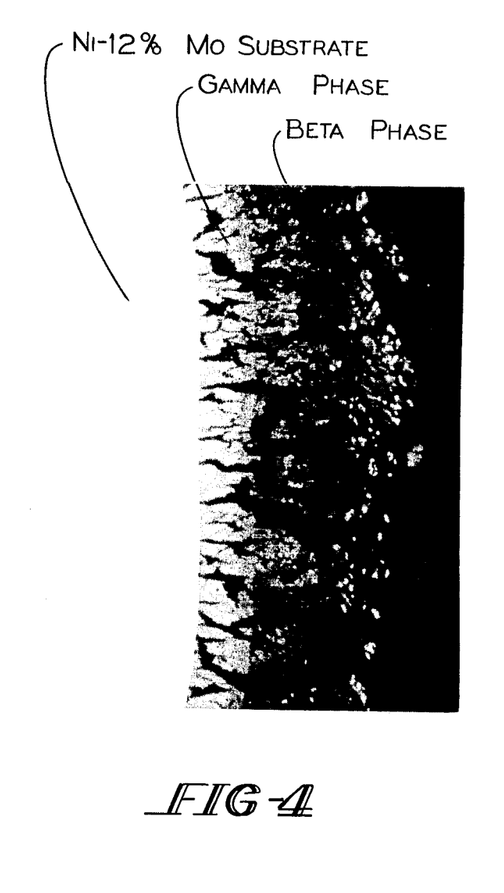
FIG. 4 is a 750× enlargement of a section of the Raney coating of FIG. 3.

The formation of the desired integral nickel-molybdenum-aluminum Beta structured ternary alloy layer is followed by a selective leaching step (22), wherein sufficient aluminum is removed to form an active Raney surface layer. For this, a strong aqueous base, such as NaOH, KOH or other strongly basic solution capable of dissolving aluminum, is generally used. Preferably, leaching is carried out with an aqueous caustic solution containing about 1 to about 30 weight percent NaOH. A preferred selective leaching procedure for producing porous nickel surfaces of the invention is carried out first for about 2 hours with 1 percent NaOH, then for about 20 hours with about 10 percent NaOH, both of these substeps being under ambient conditions in which temperature is not controlled, and finally for about 4 hours with about 30 percent NaOH at about 100° C. This leaching procedure removes at least about 60 percent, and preferably between about 75 to about 95 percent, of the aluminum from the interdiffused alloy layer and as shown in FIGS.. 3 and 4 provides a porous surface of unusually high catalytic activity. It is recognized that the leaching conditions can be varied from those mentioned above to achieve equally effective selective dissolution of the aluminum.

Figures 2, 5:
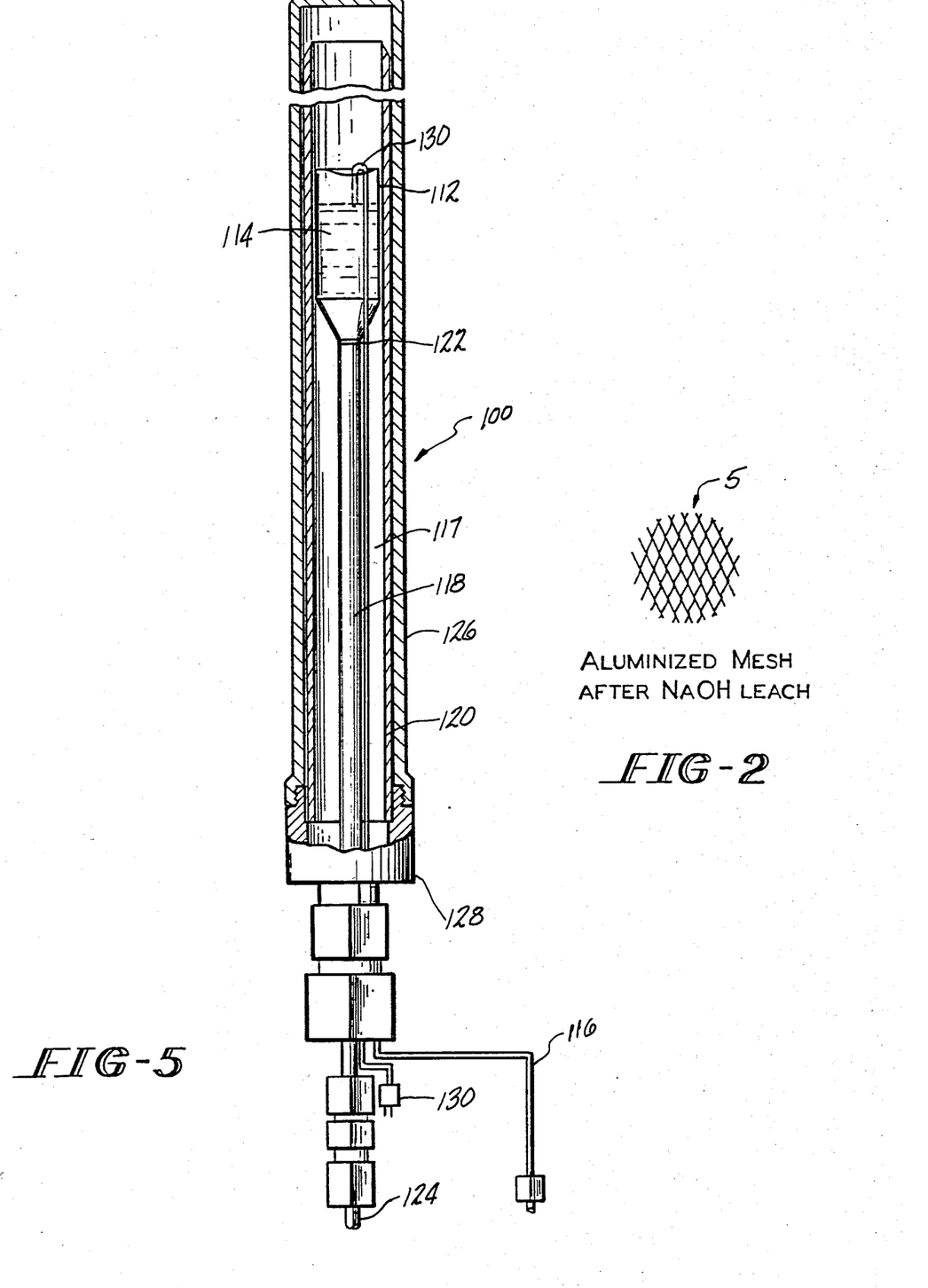
FIG. 2 shows the overall appearance of an expanded mesh embodiment of the catalyst of FIG. 1 after NaOH leaching.
FIG. 5 is a vertical cross section through an exemplary hydrogenation reactor in which the catalyst of the present invention may be used.

The appearance of catalyst (5) at this stage is shown in FIG. 2. An enlarged cross section (250×) of a strand of treated Ni-12%Mo expanded metal shown in FIG. 3 and a 750× enlargement of the porous Raney surface coating is shown in FIG. 4. In these, it is seen that the Beta structured Raney Ni-12%Mo layer is about three times as thick as the underlying Gamma layer. Since the predominant Beta layer is the outer layer which will be in contact with any medium in which the coated core is placed and is what serves to control the catalytic activity of the coating, the structure shown in FIGS. 3 and 4 is collectively called a Beta Raney Ni-12%Mo coating.

After the selective leaching, the active nickel alloy coatings may exhibit a tendency to heat up when exposed to air. If uncontrolled, this self-heating or pyrophoric tendency can easily lead to problems with coating ignition with consequent severe damage to the coating. However, chemically treating (24) the porous nickel alloy layer has been found to eliminate this problem. Convenient methods for this chemical treatment include immersing the porous nickel alloy for between about 1 hour and about 4 hours in a dilute aqueous solution of an oxidant containing, for example, by weight either (a) 3 percent $NaNO_3$, or
(b) 3 percent $K_2Cr_2O_7$, or
(c) 3 percent $NaClO_3$ and 10 percent NaOH, or
(d) 3 percent $H_2O_2$.

This treatment safely eliminates the self-heating tendency of the porous nickel alloy surface without diminishing either its catalytic activity or mechanical properties.

Lastly, before the catalyst is used for the first time, it may have to be "activated" to remove any oxidation products which may coat the surface and cause some degree of deterioration of its catalytic properties. This can be done by treating the catalyst with a flowing stream of dry hydrogen at a temperature of between about 250° C. and 350° C. for a time of between about 2 and about 24 hours. Most conveniently, this operation is done in the reactor system before the first operation so that the activated catalyst need not risk an accidental exposure to air.

Hydrogenation (1) Vapor Phase Aromatic to Alicyclic Ring Conversion

Referring now to FIG. 5, an exemplary vapor phase hydrogenation reactor (100) is shown in a cross sectional view in which a catalyst of this invention can be used. Reactor (100) comprises at least one reaction chamber (112) into which a plurality of layers (114) of catalyst (5) according to the present invention are loosely stacked, said layers being arranged so that the open structure of the mesh substrate is randomly oriented. A saturated mixture of hydrogen and the vapor of an aromatic compound such as benzene, toluene, xylene and the like is admitted to the interior of reactor (100) through gas inlet (116). The vapor is formed by passing the hydrogen through a saturator (not shown) containing the compound to be hydrogenated. Where the material has a relatively low boiling point (i.e. below about 160° C. room temperature saturation can be used. Such materials would include benzene, toluene, xylene, ethyl benzene, propyl benzene, methyl ethyl benzene, diethyl benzene, and the like.

Where the room temperature condition of material is a solid, such as with naphthalene or diphenyl or a higher boiling point liquid such as benzene having an aliphatic side chain of between about 4 and about 9 carbon atoms, saturation can be performed at higher temperatures to increase the vapor pressure of the reactive material vaporizing into the flowing stream of hydrogen. Under these conditions, the reaction, once started, is quickly driven to completion.

For vapor phase reactions, essentially 100% conversion is achieved with space velocities of up to about 3600 $hr^{-1}$ or about 500 ml/gm-hr. The entering gas passes through annulus (117) which is between discharge tube (118) and inner jacket (120) to enter the top of reaction chamber (112) and pass therethrough, contacting catalyst layers (114) and reacting enroute to form the saturated alicyclic compound corresponding to the aromatic compound entering the reactor. The open catalyst structure presents a relatively low impedance to the gas so that the observed pressure drop through the reactor is quite small. This low pressure drop combined with the high reactivity of the catalyst allows extremely high gas-flow rates through the system.

The reaction products pass first through porous filter (122) at the bottom of reaction chamber (112) to remove any solid particles present and then leave the reactor through discharge tube (118) and gas outlet (124). Such an arrangement allows the incoming gas to be heated while the reaction products are cooled. The overall reactor system is surrounded by an outer pressure jacket (126) which is sealingly mated with coupling (128) to hold all the parts in alignment and keep the system pressure tight. Temperatures within the reactor are measured by thermocouple (130). After the gases pass out of reaction chamber (112), through gas outlet (124), they are fed into a recovery system (not shown) wherein the hydrogenated products formed are separated and recovered from the reactants. Unreacted materials, mostly hydrogen, may be recycled back into the reactor as fresh feedstock.

As shown, reactor (100) does not have an inherent or self-heating capability to start the reaction. Reactor (100) is adapted to have external heating means, such as a furnace (not shown), placed around it so as to provide a controlled source of heat to the gases flowing in annulus (117) and to allow overall temperature of the system to be slowly raised until the gases start to react in reaction chamber (112). In larger applications, this temperature could be reached by preheating the incoming gases prior to their entering the system. This need not be a major problem since, with the catalyst of this invention, the hydrogenation reactions of interest generally occur at very low temperatures, relatively speaking. For example, it has been found that the conversion of lower boiling point compounds such as benzene, toluene and xylene to the corresponding saturated alicyclic compound is essentially complete, with little or no occurrence of ring cracking or other degradative reactions at temperatures in the range of about 29° C. to about 47° C. and an overall system pressure in the range of about 40 and about 60 p.s.i. These reaction conditions are substantially milder than those normally quoted for systems of this type. The ability to operate under these conditions is highly advantageous since it permits a considerable economy in the design of a full-sized system for vapor phase hydrogenation as described herein. Where higher boiling materials are involved an external preheater (not shown) may be required.

In the system shown, an equilibrium or isothermal condition was quickly established which was sustained, without difficulty, for extended periods without a need to internally cool the reacting gases. It was further found that the problems noted in the prior art in stabilizing the reactor to prevent the formation of coke and consequent plugging of the catalyst surface did not occur. This is because at the rates of gas-flow through the catalyst used, the heat sinking of the excess hydrogen makes the reaction essentially self-quenching once it passes through catalyst stack (114)

Figure 6:
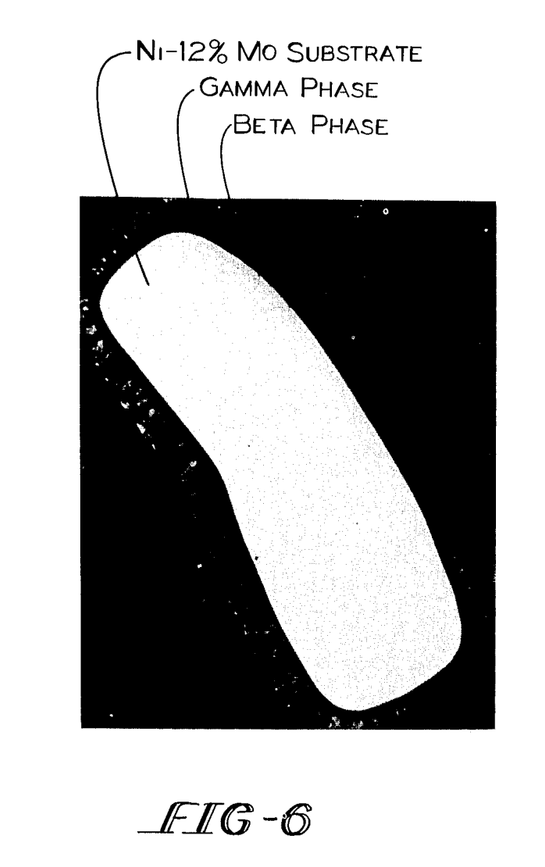
FIG. 6 is a 150× photomicrograph of the catalyst of FIG. 2 as it appeared after 259 hours of catalytic use showing the Raney coating still largely intact with substantially no coke formation on the coating
Figure 7:
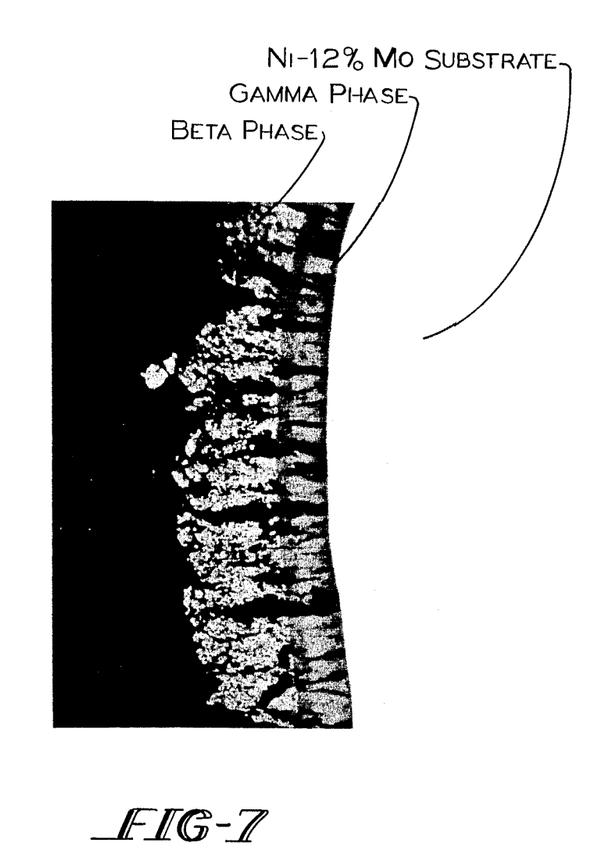
FIG. 7 is a 750× enlargement of a section of the Raney coating of FIG. 6.

FIG. 6 is a photograph of a 150× enlargement of a strand of the catalyst of the present invention after 259 hours of use in the cell of FIG. 5 in a catalytic reaction involving a wide variety of starting materials and operating conditions. FIG. 6 shows that the surface is substantially free of carbon and that the overall thickness of the coating has not been materially reduced from its thickness prior to use. These effects are more clearly shown in FIG. 7 which is a 750× magnification of the coating of FIG. 6.

One problem frequently encountered with many Raney catalysts is their high sensitivity to sulfur contamination as either $H_2S$ or $SO_2$, in the feedstock. In many commercial Raney nickel catalysts, tolerance values as low as 0.1 part per million have been quoted. The catalyst of this invention has been shown to tolerate the presence of substantially higher values of sulfur in either form, as compared to commercial catalysts now in use, without being poisoned for continued use.

Another problem often found with prior art hydrogenation catalysts is that they are adversely affected by CO in the reactive stream. However, the catalyst of this invention has been found to effectively convert CO to $CH_4$ at temperatures above about 200° C. without adverse effects upon the catalyst of this invention. At these temperatures, while CO conversion may be competitive, insofar as hydrogen is concerned, the long-term utility of the catalyst is not adversely affected.

(2) Liquid Phase R—$NO_2$ to R—$NH_2$ Conversion

In addition to the superior performance characteristics of the catalyst of the present invention in vapor phase reactions, it is also found that similar advantages are obtainable in liquid phase reactions, particularly for the conversion of aromatic nitro compounds to the corresponding amines.

For example, it is found that when about 0.05 mol of dinitrotoluene (DNT) dissolved in about 4 mols of methanol are charged into a high pressure reactor such as a Parr autoclave the dinitrotoluene is substantially completely converted to toluenediamine (TDA) at reactor temperatures in the range of about 50° C. to about 100° C. with hydrogen pressures in the range of about 160 to about 450 p.s.i., when the catalyst of this invention is employed. Typical examples of other aromatic nitro compounds which may be converted in accordance with the techniques and catalyst of this invention include nitrobenzene, dinitrobenzene, nitro toluene, trinitrotoluene, tetranitrodiphenyl ethane, nitro substituted xylenes, p,p' bis(nitrophenyl)methane, hydroxy substituted aromatic nitro compounds such as dinitrocresol, mixtures thereof and the like. The solvent component of the reactor may be any inert solvent for the nitro compound being converted. In addition to methanol, typical examples of suitable inert solvents include ethanol, ethyl acetate, dioxane, cyclohexane, 2-ethoxyethanol-1-dimethyl formamide, butyl acetate, dibutyl phthalate, glycol ethers such as ethylene glycol, dimethyl ether, mixtures thereof and the like. If desired, an aromatic amine corresponding to the aromatic nitro reactant may be employed as the solvent, but generally better results are obtained when another inert solvent is used.

The solute/solvent ratio will depend upon the solubility of the solute in the solvent. Generally speaking, it is desirable to utilize a saturated solution with flow rate and/or catalyst quantity being adjusted to assure adequate catalyst contact time to complete the reaction. In batch processes involving a fixed quantity of solution in a closed container, the same types of adjustments would apply to assure completion of the reaction. For DNT to TDA conversion batch operation, the reaction takes between about 30 and about 90 minutes depending on the temperature, hydrogen pressure and quantity of catalyst used.

It has also been found that if the operating pressure is raised to between about 800 and about 1400 p.s.i. at a temperature of between about 175° C. and about 400° C., it is possible to hydrogenate the underlying benzene ring in aromatic amines such as toluenediamine and produce such products as diaminomethylcyclohexane (DAMCH). This ability for a Raney catalyst is quite surprising since such reactions are normally performed with noble metal, i.e. platinum-based, catalysts. This reaction appears to be quite specific in that there is no evidence of ring cracking or other degradative reactions.

To avoid poisoning the catalyst in these reactions, it is necessary that the hydrogen be admitted to the reactor before it is charged with the reactant solution.

Advantages of This Invention

The catalyst of this invention offers a number of advantages when compared to prior art granular or supported Raney nickel based catalysts. Thus, as shown by the Examples, it is equally adept in promoting both vapor and liquid phase reactions so that considerable versitility in the mode of application is possible. Further, the markedly reduced sensitivity to both CO and sulfur as compared to present day Raney catalysts greatly increases the utility of this catalyst.

There are other operational advantages accruing from the use of the mesh type catalyst of the present invention for hydrogenation. At present, most, if not all, commercial systems for converting dinitrotoluene to toluenediamine employ a granular catalyst within a stirred reactor. This granular catalyst must be separated and recovered for reuse, either by an external or internal filtration system built into the process stream. This requirement adds to both the expense and complexity of building and operating the system. Further, the constant abrasion of the catalyst particles against each other will eventually reduce them to a size where they are either ineffective or nonfilterable, so periodic shutdowns, on the order of about once a year, must be scheduled to replace the catalyst. In large installations wherein several reactors are in use, this may require having an extra reactor available to pick up the slack caused by such shutdowns. With the catalyst of the present invention, these problems do not occur, which results in either a higher output for the same investment or a lower investment for the same output as compared to present systems.

Another advantage of this catalyst is its surprising ability to hydrogenate aromatic nitro compounds such as DNT all the way to DAMCH. Such products are known to offer considerable promise as the starting point for urethane coatings having superior non-yellowing properties. Such an ability can introduce considerable economies into the production of these quite important saturated alicyclic amine compounds as compared to presently used processes.

Still another advantage is the ability of the catalyst to be used in pressurized systems operating as high as about 2000 p.s.i.

The following examples are given to illustrate the invention and are not deemed to be limiting thereof. All parts and percentages are by weight unless otherwise specified.

EXAMPLE 1

A catalyst was prepared as follows:

One inch diameter discs of about 0.015 inch thick Ni-12Mo alloy which had been expanded to a mesh having a diamond cell structure with dimensions of about 0.2 by 0.3 inch on a side was thoroughly cleaned by degreasing with acetone, lightly etching with 10 percent HCl, rinsing with water and, after drying, gritblasting with No. 24 grit $Al_2O_3$ at a pressure of 3.4 $kg/CM^2$ (50 p.s.i.).

The cleaned nickel molybdenum alloy discs were aluminized by applying a commercial flux and then dipping in a pot of molten aluminum at 675° for 1 minute to entirely coat the discs with aluminum. The aluminized discs were then heat-treated at about 725° C. for about 15 minutes in a nitrogen atmosphere to interdiffuse the nickel alloy and aluminum. After heat-treating, the discs were allowed to cool in a current of nitrogen for about 2 hours which produced a predominantly Beta phase structured, interdiffused layer on the surface.

The discs were then subjected to a leaching treatment in which the aluminum was selectively removed from the interdiffused layer to produce an active porous nickel-molybdenum surface on the discs. The leaching treatment comprised immersing the interdiffused discs in 20 percent NaOH at 80° C. for approximately 1 hour to dissolve away the excess aluminum and expose the catalytically active Beta phase. After leaching, the catalyst discs were first washed to remove loose material and then placed in the reactor of FIG. 5 while still wet and dried in a stream of hydrogen. They were then activated by continuing the flow of hydrogen at a temperature of about 300° C. for about 16 hours.

EXAMPLE 2

Using the catalyst of Example 1 and the reactor of FIG. 5, a disc stack height of about 2 inches having a total catalyst content of about 12 grams and solid volume of about 1.6 cc was assembled in reaction chamber (112). A saturated mixture of benzene vapor in hydrogen prepared by bubbling hydrogen through a pool of benzene at a temperature of about 25° was admitted to the reactor at a rate of about 85 cc per minute and a pressure of about 45 p.s.i. for a space velocity of about 3541 hours$^{-1}$ or 446 ml per gram-hour.

Starting at room temperature, the temperature of the reactor was gradually raised with samples being periodically taken to monitor the progress of the reaction. The results obtained show that the reaction began at a temperature of about 30° C. with benzene to cyclohexane conversion being close to 100 percent. The reactor was run in an isothermal mode at this temperature for another 24 hours after which the reaction was terminated. Analyses of the output gases showed that the conversion of benzene to cyclohexane averaged about 97 percent during the run. Examination of the catalyst showed essentially no carbon buildup or other source of degradation.

EXAMPLE 3

Using the catalyst of Examples 1 and 2, the method of Example 2 was repeated with toluene. Hydrogenation to methylcyclohexane commenced at about 27° C., reaching substantially 100 percent completion at 37° C. at which temperature the reaction was continued for about 24 hours. The catalyst was clean and free of coke and there was no apparent deterioration of catalytic activity with time.

EXAMPLE 4

Using the catalyst of Examples 1, 2 and 3, the method of Example 2 was repeated with xylene. Hydrogenation to dimethylcyclohexane commenced at 28° C., reaching substantial completion at 47° C. at which temperature the reaction was continued for about 48 hours. The catalyst was clean and free of coke and no deterioration of catalytic activity with time was observed.

EXAMPLE 5

The method of Example 1 was used to prepare a catalyst containing a Raney Ni-5%Ru Beta structured surface thereon. This was placed in reaction chamber (112) of the reactor of FIG. 5 and the method of Example 2 was repeated. Conversion of benzene to cyclohexane started at about 24° C. and reached substantially 100 percent in a temperature range of between 86° C. and 90° C. The reactor was run in this temperature range for a total of 50 hours after which an inspection of the catalyst showed no apparent degradation or coke formation on the surface.

EXAMPLES 6-8

A 300 ml capacity Parr autoclave with 19 grams of the catalyst of Example 1 which had been preactivated at 300° C. in flowing hydrogen for 16 hours was used for these examples. The autoclave contained a stirrer and the catalyst discs were fabricated with a central hole in the mesh sufficient to allow the shaft of the stirring rod to fit loosely therethrough. The catalyst discs were not coupled to the shaft and except for some frictionally induced motion did not turn with it.

The reactor was pressurized with hydrogen and then charged with about 9.1 grams (0.05 mol) of 2-4 dinitrotoluene dissolved in 150 ml of methanol and after which stirring was commenced and the system brought up to temperature. Progress of the reaction was observed by monitoring the change in hydrogen pressure as the reaction proceeded with additional hydrogen being periodically added to replace that removed by amination. The reaction was considered to be completed when not further reduction in hydrogen pressure was observed. Condition of temperature, pressure and reaction time are given in Table I below.

TABLE I

| Example | Temp. (°C.) | Pressure (p.s.i.) | Reaction Time (Min.) |
|---------|-------------|-------------------|----------------------|
| 6 | 100 | 350-450 | 32 |
| 7 | 70 | 160-220 | 65 |
| 8 | 50 | 160-220 | 97 |

Analyses of the reaction product by gas chromatography showed that in all three examples essentially 100 percent conversion of dinitrotoluene to toluenediamine occurred.

The reaction products were identified by mass spectroscopic analyses. No evidence of ring cracking was observed.

This invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. In a method for hydrogenating an aromatic ring compound of the type wherein K is either benzene or napththalene, $R_1$ is hydrogen atom or an aliphatic chain containing from about 1 to about 9 carbon atoms or a phenyl radical, $R_2$ is a hydrogen atom or an aliphatic chain containing from about 1 to about 3 carbon atoms, and $R_3$ and $R_4$ are hydrogen atoms, hydroxy, or nitro groups in the presence of catalyst, said catalyst comprising a structure comprised of a Raney metal alloy surface layer integral with and derived from a selected nickel alloy monolithic substrate mesh structure, wherein said surface layer is predominantly derived from an adherent $Ni_xM_{1-x}Al_3$ Beta phase structured crystalline precursory layer, where M is a catalytic activator selected from the group consisting of molybdenum, titanium, tantalum, ruthenium or mixtures thereof, and where x, the fraction of nickel in combined weight of Ni and M, is within the range of from about 0.80 to about 0.95.

2. The method of claim 1 wherein said catalytic activator is molybdenum.

3. A method for hydrogenating an aromatic ring compound of the type wherein K is either benzene or naphthalene, $R_1$ is a hydrogen atom or an aliphatic chain containing from about 1 to about 9 carbon atoms or a phenyl radical, $R_2$ is a hydrogen atom or an aliphatic chain containing from about 1 to about 3 carbon atoms, and $R_3$ and $R_4$ are hydrogen atoms, or hydroxy, groups which comprises:

(a) admixing hydrogen with said compound to form a mixture;

(b) preheating said mixture and passing it through a catalyst, said catalyst comprising a plurality of metallic mesh plates, each of said plate comprising a selected nickel alloy monolithic substrate mesh core structure and a Raney metal alloy surface layer integral with and derived from said core structure, wherein said surface layer is predominantly derived from an adherent $Ni_xM_{1-x}Al_3$ Beta phase structured crystalline precursory layer, where M is a catalytic activator selected from the group consisting of molybdenum, titanium, tantalum, ruthenium or mixtures thereof, and where x, the fraction of nickel in the combined weight of Ni and M, is within the range of from about 0.80 to about 0.95, whereby said mixture exothermally reacts to form a reaction product when contacted with said catalyst; and (c) recovering said reaction product.

4. The method of claim 1 or 3 wherein said mesh core comprises an alloy of nickel and a catalytic activator, said alloy containing between about 80 and about 95% nickel by weight.

5. The method of claim 4, wherein said catalytic activator is selected from the group consisting of molybdenum, ruthenium, tantalum, titanium, or mixtures thereof.

6. The method of claim 3 wherein said catalyst is formed by the steps comprising:
(a) coating the surfaces of a clean, non-porous metal base mesh structure of a nickel base alloy having from about 5 to about 20 percent of a catalytic activator therein with aluminum;
(b) heating said coated mesh surfaces to a temperature of from about 660° C. to about 750° C. for a time sufficient to infuse a portion of said aluminum into the outer portions of said mesh structure so as to form said integral adherent Beta structured crystalline precursory layer in its outer portions; and
(c) leaching out residual aluminum from said outer portion until said Raney metal exterior surface is formed integral with said mesh structure.

7. The method of claim 3 wherein said catalyst activator is molybdenum.

8. The method of claim 3 wherein said catalyst activator is ruthenium.

9. The method of claim 3 wherein said catalyst activator is tantalum.

10. The method of claim 3 wherein said catalyst activator is titanium.

11. The method of claim 7 wherein $1-x$ is between about 0.10 and about 0.18.

12. The method of claim 8 wherein $1-x$ is between about 0.05 and about 0.1.

13. The method of claim 3 wherein the hydrogen in said mixture is saturated with said aromatic ring compound.

14. The method of claim 3 wherein said admixing is done by saturating a flowing stream of gaseous hydrogen with said aromatic ring compound, said hydrogenation reaction occurring when said flowing stream passes through said mesh catalyst.

15. The method of claim 14 wherein said aromatic ring compound is benzene.

16. The method of claim 14 wherein said aromatic ring compound is toluene.

17. The method of claim 14 wherein said aromatic ring compound is xylene.

18. The method of claim 14 wherein said aromatic ring compound is naphthalene.

19. The method of claim 14 wherein said aromatic ring compound is diphenyl.

20. The method of claim 14 wherein said hydrogenating is effected at a pressure in the range between about 50 and about 100 p.s.i.

21. The method of claim 14 wherein said preheat temperature is between about 25° C. and about 200° C.

22. The method of claim 14 wherein said equilibrium temperature is between about 30° C. and about 400° C.

23. The method of claim 3 wherein a further step comprises dissolving said compound in an inert solvent to form a solution and admixing said solution with hydrogen, said hydrogenation occurring when said admixed solution is contacted with said mesh catalyst.

24. The method of claim 23 wherein said hydrogenation is effected at a pressure in the range between about 40 and about 2000 p.s.i.

25. The method of claim 24 wherein said preheat temperature is between about 25° C. and about 200° C.

26. The method of claim 24 wherein said equilibrium temperature is between about 30° C. and about 400° C.

27. The method of claim 23 wherein said aromatic ring compound is dinitrotoluene.

28. The method of claim 23 wherein said aromatic ring compound is dinitrobenzene.

29. The method of claim 23 wherein said aromatic ring compound is p,p'-bis(nitrophenylmethane).

30. The method of claim 3 further comprising the step of activating said catalyst prior to its first use.

31. The method of claim 30 wherein said activation comprises heating said catalyst in a flowing stream of gaseous hydrogen for a time between about 2 and about 24 hours at a temperature between about 250° C. and about 350° C.

32. In a reactor of claim 32 wherein an aromatic ring compound of the type wherein K is either benzene or napthalene, $R_1$ is a hydrogen atom or an aliphatic chain containing from about 1 to about 9 carbon atoms or a phenyl radical, $R_2$ is a hydrogen atom or an aliphatic chain containing from about 1 to about 3 carbon atoms, and $R_3$ and $R_4$ are hydrogen atoms, hydroxy or nitro groups is hydrogenated in the presence of a catalyst, said catalyst comprising a structure comprised of a Raney metal alloy surface layer integral with and derived from a selected nickel alloy monolithic substrate mesh structure, wherein said surface layer is predominantly derived from an adherent $Ni_xM_{1-x}Al_3$ Beta phase structured crystalline precursory layer, where M is a catalytic activator selected from the group consisting of molybdenum, titanium, tantalum, ruthenium or mixtures thereof, and where x, the fraction of nickel in the combined weight of Ni and M, is within the range of from about 0.80 to about 0.95, said reactor comprising a reaction chamber containing a plurality of said mesh structures, means for feeding a mixture of hydrogen and said aromatic compound into said reactor to contact said mesh structure at a temperature and pressure sufficient to cause said hydrogenation reaction to occur, and means for withdrawing the reaction product from said reactor.

33. The reactor of claim 32 wherein said catalyst activator is molybdenum.

34. The reactor of claim 32 wherein said catalyst activator is ruthenium.

35. The reactor of claim 32 wherein said catalyst activator is tantalum.

36. The reactor of claim 32 wherein said catalyst activator is titanium.

37. The reactor of claim 33 wherein $1-x$ is between about 0.10 and about 0.18.

38. The reactor of claim 34 wherein $1-x$ is between about 0.05 and about 0.1.

39. The reactor of any one of claims 32 to 38 wherein said mesh core comprises an alloy of nickel and a catalytic activator, said alloy containing between about 80 and about 95% nickel by weight.

40. The reactor of claim 39 wherein said catalytic activator is selected from the group consisting of molybdenum, ruthenium, tantalum, titanium, or mixtures thereof.

* * * * *

UNITED STATES PATENT AND TRADEMARK OFFICE
CERTIFICATE OF CORRECTION

PATENT NO.  : 4,513,149

DATED       : April 23, 1985

INVENTOR(S) : Thomas J. Gray and Norman G. Masse

It is certified that error appears in the above-identified patent and that said Letters Patent is hereby corrected as shown below:

In column 4, line 28, after "the" delete "desrred" and insert --desired--.

In column 5, line 52, after "metal" insert --is--.

In column 6, line 44, after "$^{O}C$" insert --)--.

In column 8, line 46, after "of the" insert --solution in the--.

In column 11, line 43, delete "Condition" and insert --Conditions--.

In claim 1, line 27, after "in" insert --the--.

In claim 3, line 48, after "atoms," delete "or hydroxy, groups" and insert --hydroxy, or nitro groups--.

In claim 23, line 62, after "hydrogenation" insert --reaction--.

In claim 32, line 15, after "reactor" delete "of claim 32".

Signed and Sealed this

Twenty-fifth Day of March 1986

[SEAL]

Attest:

DONALD J. QUIGG

Attesting Officer

Commissioner of Patents and Trademarks